(12) United States Patent
Parris

(10) Patent No.: US 10,010,572 B2
(45) Date of Patent: Jul. 3, 2018

(54) COMPOSITION FOR MUSCULOSKELETAL PAIN

(71) Applicant: Winston C. V. Parris, Durham, NC (US)

(72) Inventor: Winston C. V. Parris, Durham, NC (US)

( * ) Notice: Subject to any disclaimer, the term of this patent is extended or adjusted under 35 U.S.C. 154(b) by 151 days.

(21) Appl. No.: 14/838,567

(22) Filed: Aug. 28, 2015

(65) Prior Publication Data
US 2017/0056464 A1 Mar. 2, 2017

(51) Int. Cl.
A61K 36/00 (2006.01)
A61K 36/61 (2006.01)
A61K 36/889 (2006.01)
A61K 36/53 (2006.01)
A61K 36/57 (2006.01)
A61K 31/125 (2006.01)
A61K 31/621 (2006.01)
A61K 9/00 (2006.01)
A61K 47/06 (2006.01)
A61K 9/10 (2006.01)
A61K 31/165 (2006.01)
A61K 31/196 (2006.01)

(52) U.S. Cl.
CPC ............ *A61K 36/61* (2013.01); *A61K 9/0014* (2013.01); *A61K 9/10* (2013.01); *A61K 31/125* (2013.01); *A61K 31/165* (2013.01); *A61K 31/196* (2013.01); *A61K 31/621* (2013.01); *A61K 36/53* (2013.01); *A61K 36/57* (2013.01); *A61K 36/889* (2013.01); *A61K 47/06* (2013.01)

(58) Field of Classification Search
CPC .................................................... A61K 36/00
See application file for complete search history.

(56) References Cited

U.S. PATENT DOCUMENTS

| 4,657,933 A * | 4/1987 | Collins ................ A61K 9/0014 514/722 |
| 2007/0082071 A1* | 4/2007 | Willimann ............ A61K 9/0043 424/727 |
| 2010/0021563 A1* | 1/2010 | Levesque ................ A61K 8/27 424/642 |
| 2010/0189668 A1* | 7/2010 | McCullough ........ A61K 9/0014 424/60 |
| 2014/0134261 A1* | 5/2014 | Singh ..................... A61K 31/22 424/522 |

OTHER PUBLICATIONS

Benson GD., "Acetaminophen in Chronic Liver Disease", Clin Pharmacol Ther. (1983), vol. 33, pp. 95-101.
Liew et al, "Acetaminophen Use During Pregnancy, Behavioral Problems and Hyperkinetic Disorders", Jama. Pediatr. (2014), vol. 169(4), pp. 313-320.
Fitzgerald GA, "Coxibs and Cardiovascular Disease", New England Journal of Medicine (2004), vol. 351, pp. 1709-1711.
Furberg et al., "Parecoxib, Valdecoxib, and Cardiovascular Risk", Circulation (2005), vol. 111, pp. 249.
Cheng et al., "Cyclooxygenases, the Kidney, and Hypertension", Hypertension (2004), vol. 43, pp. 525-530.
Trescot et al., "Opioid Guidelines in the Management of Chronic Non-Cancer Pain", Pain Physician (2006), vol. 9, pp. 1-40.
Manchikanti et al., "Controlled Substance Abuse and Illicit Drug Use in Chronic Pain Patients: An Evaluation of Multiple Variables", Pain Physician (2006), vol. 9, pp. 215-225.
Compton et al., "Abuse of Prescription Drugs and the Risk of Addiction", Drug Alcohol Depend (2006), vol. 83(suppl.1), pp. S4-S7.
Pasternak GW, "Molecular Biology of Opioid Analgesia," J Pain Symptom Manage (2005), vol. 29(5 suppl), S2-S9.
https://www.youtube.com/watch?v=hcDqwuqDPso, published Mar. 5, 2015.

* cited by examiner

*Primary Examiner* — Qiuwen Mi
(74) *Attorney, Agent, or Firm* — Brinks Gilson & Lione

(57) ABSTRACT

Described herein are compositions and methods of treatment for musculoskeletal pain.

11 Claims, No Drawings

COMPOSITION FOR MUSCULOSKELETAL PAIN

TECHNICAL FIELD

Described herein are compositions and methods of treatment for musculoskeletal pain comprising essential oils and active agents.

BACKGROUND

Chronic pain syndromes and their associated management have dominated the medical landscape for the past three decades. While great progress has been made in chronic pain management, there is no outstanding drug that reliably relieves chronic pain without unacceptable complications and/or adverse effects. This is particularly true in the management of chronic musculoskeletal pain syndromes.

Musculoskeletal pain and myofascial pain are very common in most societies and in most countries. These pains are derived usually from traumatic injuries, inflammatory lesions, various arthritic processes, postural, athletic and occupational events and in older persons, a simple consequence of the degenerative aging process. Whereas all pain regardless of etiology is unpleasant and is usually associated with negative perceptions and emotions, pain, especially chronic pain, should never be considered benign. The pain associated with progressive pancreatic cancer or metastatic lung or breast cancer, for example, may be appropriately labelled as malignant pain because these pains may be associated with death and the dying process. The pain of non-neoplastic musculoskeletal lesions, however, should not be labelled as benign: a characterization of non-malignant chronic pain is more appropriate.

The treatment of non-malignant, chronic musculoskeletal pain may be holistic and conservative; interventional; or pharmacological. The holistic or conservative measures include exercise, diet management, physical therapy, coordinated chiropractic measures, acupuncture and appropriate complementary non-invasive measures. The interventional measures used to treat non-malignant, chronic musculoskeletal pain should be few and seldom needed or used. Occasionally, selected peripheral nerve blocks may be indicated but major procedures or surgical interventions are seldom warranted.

The pharmacological treatment of non-malignant, chronic musculoskeletal pain involves the use of topical analgesic agents and oral analgesic adjuvants including non-steroidal anti-inflammatory drugs, COX-2 inhibitors, gabapentinoids, narcotic analgesics, and other drugs. All these drugs have potential side effects and complications. Acetaminophen, which is commonly used for musculoskeletal pain, may cause irreversible hepatic disease in some patients and only recently was shown to be associated with ADHD (Attention Deficit Hyperactive Disorder) in the children of patients who took that drug during gestation. See, Benson, G D. *Clin Pharmacol Ther.* 33:95-101 (1983) and Liew et al., *Jama. Pediatr.* 168(4): 313-320 (2014), each incorporated by reference with regard to the noted teaching. Non-steroidal anti-inflammatory drugs (NSAIDS) gained popularity, but the resultant gastrointestinal complications associated with costly hospitalization and even death have curtailed their use. See, Fitzgerald G A, *New Engl J Med.* 351:1709-1711 (2004). Furberg et al., *Circulation.* 111:249 (2005), incorporated by reference with regard to the noted teaching. Hepatic and renal complications may also occur with use of known analgesic drugs. See, Cheng et al., *Hypertension.* 43:525-530 (2004), incorporated by reference with regard to the noted teaching.

In recent times, the consequences of inappropriate use of narcotic analgesic drugs have become so serious in the US that both state and federal governments are taking active and definitive measures to deal with those issues which are assuming national importance. Drug addiction, habituation, dependency, drug abuse, drug misuse, drug diversion, and drug overdose are all too common and the resulting challenges are becoming major national, social, legal, cultural and economic issues of this decade. See, e.g., Trescot et al., *Pain Physician.* 9:1-40 (2006) and Manchikanti et al., *Pain Physician.* 9:215-225 (2006), incorporated by reference with regard to the noted teaching. The risk to all socioeconomic segments of society dying from the complications of opioid abuse and misuse is alarming. In many instances, these persons initially began using opioids for relatively trivial musculoskeletal or myofascial lesions and then progressed to more potent drugs and larger doses. See, e.g., Compton et al., *Drug Alcohol Depend.* 83(suppl. 1):S4-S7(2006), incorporated by reference with regard to the noted teaching. Further, opioids may also cause early and late respiratory depression, constipation, pruritus, and urinary retention. See, e.g., Pasternak G W. *J Pain Symptom Manage.* 29(5 suppl):S2-S9 (2005), incorporated by reference with regard to the noted teaching.

In St. Lucia, the Caribbean, and many other parts of the world, it has been well-known that coconut oil has many dietary, therapeutic, and analgesic properties. Whereas, there is very scant scientific evidence to support those claims, most indigenous inhabitants of those tropical and subtropical countries embrace and practice that belief. Thus, a novel composition including essential oils, like coconut oil, which has both analgesic and anti-inflammatory properties without harmful side effects, could prove to be efficacious as a topical analgesic in the management of chronic musculoskeletal and myofascial pain. Such a composition is currently commercially available in St. Lucia and sold as "Fidapin".

SUMMARY

One embodiment described herein is a composition for musculoskeletal pain comprising: (a) about 35-45% by weight of at least one carrier oil; (b) about 55-65% by weight of at least three essential oils. One embodiment of the present invention optionally includes about 5-10% by weight of at least one active agent.

In one aspect described herein, the carrier oil ingredient comprises one or more of mineral oil, white oil, liquid paraffin, liquid petroleum, almond oil, aloe vera oil, apricot kernel oil, avocado oil, calendula oil, primrose oil, grape seed oil, hazelnut oil, jojoba oil, macadamia oil, rosehip oil, sesame oil, walnut oil, wheatgerm oil or combinations thereof.

In another aspect described herein, the essential oils comprises one or more of agar oil, ajwain oil, angelica root oil, anise oil, asafoetida, Balsam of Peru, basil oil, bay oil, Bergamot oil, black pepper, birch oil, camphor, cannabis flower, caraway oil, cardamom seed oil, carrot seed oil, cedarwood oil, chamomile oil, calamus Root, cinnamon oil, cistus species, citron, citronella oil, clary sage, clove leaf oil, refined coconut oil, coffee, coriander, costmary oil (bible leaf oil), costus root, cranberry seed oil, cubeb, cumin oil/black seed oil, cypress, cypriol, curry leaf, davana oil, dill oil, elecampane, eucalyptus oil, fennel seed oil, fenugreek oil, fir, frankincense oil, galangal, galbanum, geranium oil, ginger oil, goldenrod, grapefruit oil, henna oil, helichrysum, hickory nut oil, horseradish oil, hyssop, Idaho tansy, jasmine oil, juniper berry oil, laurus nobilis, lavender oil, ledum, lemon oil, lemongrass, lime, litsea cubeba oil, linaloe, mandarin, marjoram, melaleuca, Melissa oil (lemon balm), mentha arvensis oil/mint oil, methyl salicylate (sweet birch, wintergreen, or teaberry), moringa oil, mountain savory, mugwort oil, mustard oil (essential oil), myrrh oil, myrtle, neem oil or Neem Tree Oil, neroli, nutmeg oil, orange oil, oregano oil, orris oil, Palo Santo, parsley oil, Patchouli oil, Perilla essential oil, peppermint oil, petitgrain, pine oil, Ravensara, Red Cedar, Roman Chamomile, rose oil, rosehip oil, rosemary oil, rosewood oil, sage oil, sandalwood oil, sassafras oil, savory oil, Schisandra oil, spearmint oil, spikenard, spruce, star anise oil, tangerine, tarragon oil, tea tree oil, thyme oil, Tsuga, turmeric, valerian, vetiver oil (khus oil), Western Red Cedar, wintergreen, ylang-ylang, zedoary or combinations thereof.

In another aspect described herein, the active agent ingredient comprises one or more of capsaicin, diclofenac, magnesium salicylate, acetylsalicylic acid, or combinations thereof.

In another aspect described herein, the composition comprises: (a) about 35-45% mineral oil; (b) about 35-45% refined coconut oil; (c) about 1-8% eucalyptus oil; (d) about 1-10% nutmeg oil; (e) about 0.5-5% rosemary oil; (f) about 0.5-5% camphor; and (g) about 1-8% methyl salicylate. In another aspect described herein, the composition further comprises about 1-5% clove oil. In another aspect described herein, the composition comprises: (a) about 40% mineral oil; (b) about 40% refined coconut oil; (c) about 4% eucalyptus oil; (d) about 5.61% nutmeg oil; (e) about 2.41% rosemary oil; (f) about 1% clove oil; (g) about 2.41% camphor; and (h) about 4.81% methyl salicylate. In another aspect described herein, the composition comprises: (a) about 38.9% mineral oil; (b) about 40.3% refined coconut oil; (c) about 4% eucalyptus oil; (d) about 5.61% nutmeg oil; (e) about 2.41% rosemary oil; (f) about 1.6% clove oil; (g) about 2.41% camphor; and (h) about 4.81% methyl salicylate. In another aspect described herein, the ratio of carrier oil to essential oils comprises from about 0.5:1 to about 1:1. In another aspect described herein, the composition is suitable for topical application. In another aspect described herein, the ratio of coconut oil to rosemary oil is about 16:1 to 17:1. In another aspect described herein, the composition comprises six or more essential oils.

Another embodiment described herein is a method for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition comprising: (a) about 35-45% mineral oil; (b) about 35-45% refined coconut oil; (c) about 1-8% eucalyptus oil; (d) about 1-10% nutmeg oil; (e) about 0.5-5% rosemary oil; (f) about 0.5-5% camphor; and (g) about 1-8% methyl salicylate.

Another embodiment described herein is a method for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition comprising: (a) about 40% mineral oil; (b) about 40% refined coconut oil; (c) about 4% eucalyptus oil; (d) about 5.61% nutmeg oil; (e) about 2.41% rosemary oil; (f) about 1% clove oil; (g) about 2.41% camphor; and (h) about 4.81% methyl salicylate.

Another embodiment described herein is a method for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition comprising: (a) about 38.9% mineral oil; (b) about 40.3% refined coconut oil; (c) about 4% eucalyptus oil; (d) about 5.61% nutmeg oil; (e) about 2.41% rosemary oil; (f) about 1.6% clove oil; (g) about 2.41% camphor; and (h) about 4.81% methyl salicylate.

In another embodiment described herein, is a composition useful for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising administering to a subject in need thereof a composition as described herein.

In another embodiment described herein, is a use of a composition for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition as described herein.

The scope of the present invention includes all combinations of aspects, embodiments, and preferences herein described.

DETAILED DESCRIPTION

Described herein are compositions for the treatment of chronic musculoskeletal pain. The compositions described herein comprise a variety of essential oils or combinations thereof and release the active agent at various rates, to provide rapid relief. Also described herein are methods for the treatment of musculoskeletal pain.

One embodiment described herein is a composition for the treatment of chronic musculoskeletal pain that is not addictive and ameliorates the risks associated with the use of opioids. One embodiment described herein is a rapid release composition for the treatment of chronic musculoskeletal pain. In another embodiment described herein, the composition comprises one or more carrier oils, one or more essential oils and one or more active agents.

The term "carrier oil" as used herein refers to the base oil in which the essential oils and active agents reside.

The term "essential oils" as used herein refers to concentrated hydrophobic liquids containing volatile aroma compounds from plants or other source, namely having the characteristic fragrance of the plant or other source. Essential oils may be extracted, such as by distillation, from the source, but certain essential oils may be synthesized commercially. Essential oils have been used medicinally throughout history, ranging from skin treatment to remedies for cancer. One embodiment of the composition of the present invention provides a unique combination of essential oils, which is demonstrated to provide an analgesic effect.

The term "active agents" as used herein refers to a pharmaceutical agent, active ingredient, compound, or substance, compositions, or mixtures thereof, that provide a pharmacological, often beneficial, effect.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "rapid onset" as used herein refers to the amount of time after application of the composition in which an analgesic effect occurs, preferably about less than 30 minutes from application.

In one embodiment described herein, a composition comprises that shown in Table 1.

TABLE 1

Exemplary Musculoskeletal Topical Composition

| Exemplary Component | Composition Weight Percent Range (%) |
|---|---|
| Carrier | 35-45 |
| Essential Oils | 55-65 |
| TOTAL | 100% |

In another embodiment described herein, a composition comprises that shown in Table 2. This composition is also referred to herein as Embodiment #1.

TABLE 2

Exemplary Musculoskeletal Topical Composition

| Component | Exemplary Component | Composition Weight Percent Range (%) |
|---|---|---|
| Carrier | Mineral Oil | 35-45 |
| Essential Oils | Refined Coconut Oil | 35-45 |
| | Eucalyptus Oil | 1-8 |
| | Nutmeg Oil | 1-10 |
| | Rosemary Oil | 0.5-5 |
| | Clove Oil | 1-5 |
| | Camphor | 0.5-5 |
| | Methyl Salicylate | 1-8 |
| TOTAL | | 100% |

In another embodiment described herein, a composition comprises that shown in Table 3. This composition is also referred to herein as Embodiment #2.

TABLE 3

Exemplary Musculoskeletal Topical Composition

| Component | Exemplary Component | Weight Percentage (%) |
|---|---|---|
| Carrier | Mineral Oil | 40.5 |
| Essential Oils | Refined Coconut Oil | 40.27 |
| | Eucalyptus Oil | 4.01 |
| | Nutmeg Oil | 5.61 |
| | Rosemary Oil | 2.41 |
| | Clove Oil | 1 |
| | Camphor | 2.41 |
| | Methyl Salicylate | 4.81 |
| TOTAL | | 100% |

In another embodiment described herein, a composition comprises that shown in Table 4. This composition is also referred to herein as Embodiment #3.

TABLE 4

Exemplary Musculoskeletal Topical Composition

| Component | Exemplary Component | Weight Percentage (%) |
|---|---|---|
| Carrier | Mineral Oil | 38.9 |
| Essential Oils | Refined Coconut Oil | 40.27 |
| | Eucalyptus Oil | 4.01 |
| | Nutmeg Oil | 5.61 |
| | Rosemary Oil | 2.41 |
| | Clove Oil | 1.6 |
| | Camphor | 2.41 |
| | Methyl Salicylate | 4.81 |
| TOTAL | | 100% |

In one embodiment described herein, the composition comprises one or more carrier oils. In one embodiment, the one or more carrier oils include those with and without fragrance. In one embodiment, the one or more carrier oils comprise mineral oil. In other embodiments, the carrier oils comprise white oil, liquid paraffin, liquid petroleum, almond oil, aloe vera oil, apricot kernel oil, avocado oil, calendula oil, primrose oil, grape seed oil, hazelnut oil, jojoba oil, macadamia oil, rosehip oil, sesame oil, walnut oil, wheatgerm oil or combinations thereof. In one aspect, the carrier oil comprises mineral oil.

In one embodiment, the one or more carrier oils comprise a weight percentage of about 35% to about 45% by weight of the composition, including each integer within the specified range. In one embodiment, the inert carrier oil comprises about 36% to about 44%, about 37% to about 43%, about 38% to about 42%, or about 39% to about 41% by weight of the composition. In one aspect, the carrier oil comprises about 35%, about 36%, about 37%, about 38%, about 39%, about 40%, about 41%, about 42%, about 43%, about 44%, or about 45% by weight of the composition. In one aspect, the carrier oil comprises about 40% by weight of composition. In one aspect, the carrier oil comprises about 38%, about 39%, or 41% by weight of the composition.

In another embodiment, the one or more carrier oils comprise mineral oil having a weight percentage of about 35% to about 45% by weight of the composition, including each integer within the specified range. In one embodiment, mineral oil comprises about 36% to about 44%, about 37% to about 43%, about 38% to about 42%, or about 39% to about 41% by weight of the composition. In one aspect, mineral oil comprises about 35%, about 36%, about 37%, about 38%, about 39%, about 40%, about 41%, about 42%, about 43%, about 44%, or about 45% by weight of the composition. In one aspect, mineral oil comprises about 40% by weight of the inert carrier oil. In one aspect, mineral oil comprises about 38%, about 39%, or about 41% by weight of the composition.

In another embodiment, the composition comprises three or more essential oils. In one embodiment essential oils comprise agar oil, ajwain oil, angelica root oil, anise oil, asafoetida, Balsam of Peru, basil oil, bay oil, Bergamot oil, black pepper, birch oil, camphor, cannabis flower, caraway oil, cardamom seed oil, carrot seed oil, cedarwood oil, chamomile oil, calamus Root, cinnamon oil, cinnamon cassia, cistus species, citron, citronella oil, clary sage, clove leaf oil, refined coconut oil, coffee, coriander, costmary oil (bible leaf oil), costus root, cranberry seed oil, cubeb, cumin oil/black seed oil, cypress, cypriol, curry leaf, davana oil, dill oil, elecampane, eucalyptus oil, fennel seed oil, fenugreek oil, fir, frankincense oil, galangal, galbanum, geranium oil, ginger oil, goldenrod, grapefruit oil, henna oil, helichrysum, hickory nut oil, horseradish oil, hyssop, Idaho tansy, jasmine oil, juniper berry oil, laurus nobilis, lavender oil, ledum, lemon oil, lemongrass, lime, litsea cubeba oil, linaloe, mandarin, marjoram, melaleuca, Melissa oil (lemon balm), mentha arvensis oil/mint oil, methyl salicylate (sweet birch, wintergreen, or teaberry), moringa oil, mountain savory, mugwort oil, mustard oil (essential oil), myrrh oil, myrtle, neem oil or Neem Tree Oil, neroli, nutmeg oil, orange oil, oregano oil, orris oil, Palo Santo, parsley oil, Patchouli oil, Perilla essential oil, peppermint oil, petitgrain, pine oil, Ravensara, Red Cedar, Roman Chamomile, rose oil, rosehip oil, rosemary oil, rosewood oil, sage oil, sandalwood oil, sassafras oil, savory oil, Schisandra oil, spearmint oil, spikenard, spruce, star anise oil, tangerine, tarragon oil, tea tree oil, thyme oil, Tsuga, turmeric, valerian, vetiver oil (khus oil), Western Red Cedar, wintergreen, ylang-ylang, zedoary or combinations thereof. In one aspect, essential oils comprise refined coconut oil, eucalyptus oil, nutmeg oil, rosemary oil, clove oil, camphor, methyl salicylate, or combinations thereof.

In another embodiment described herein, the three or more essential oils comprise a weight percentage of about 55% to about 65% by weight of the composition, including each integer within the specified range. In one embodiment, the essential oil comprises about 55% to about 65%, about 56% to about 64%, about 57% to about 63%, or about 58% to about 62% by weight of the composition. In one aspect, the essential oil comprises about 55%, about 56%, about 57%, about 58%, about 59%, about 60%, about 61%, about 62%, about 63%, about 64%, or about 65% by weight of the composition.

In another embodiment described herein, three or more essential oils comprise refined coconut oil having a weight percentage of about 35% to about 45% by weight of the composition. In one embodiment, the refined coconut oil comprises about 36% to about 44%, about 37% to about 43%, about 38% to about 42%, or about 39% to about 41% by weight of the composition. In one aspect, the refined coconut oil comprises about 35%, about 36%, about 37%, about 38%, about 39%, about 40%, about 41%, about 42%, about 43%, about 44%, or about 45% by weight of the composition. In one aspect, the refined coconut oil comprises about 40% by weight of the composition. In one aspect, the refined coconut oil comprises about 38%, about 39%, about 41%, or about 42% by weight of the composition.

In another embodiment described herein, three or more essential oils comprise eucalyptus oil having a weight percentage of about 1% to about 8% by weight of the composition. In one embodiment, the eucalyptus oil comprises about 2% to about 7%, about 3% to about 6%, or about 4% to about 5% by weight of the composition. In one aspect, the eucalyptus oil comprises about 1%, about 2%, about 3%, about 4%, about 5%, about 6%, about 7%, or about 8% by weight of the composition. In one aspect, the eucalyptus oil comprises about 4% by weight of the composition. In one aspect, the eucalyptus oil comprises about 2%, about 3%, about 5%, or about 6% by weight of the composition.

In another embodiment described herein, three or more essential oils comprise nutmeg oil having a weight percentage of about 1% to about 10% by weight of the composition. In one embodiment, the nutmeg oil comprises about 2% to about 9%, about 3% to about 8%, about 4% to about 7%, or about 5% to about 6% by weight of the composition. In one aspect, the nutmeg oil comprises about 1%, about 2%, about 3%, about 4%, about 5%, about 6%, about 7%, about 8%, about 9%, or about 10% by weight of the composition. In one aspect, the nutmeg oil comprises about 6% by weight of the composition. In one aspect, the nutmeg oil comprises about 2%, about 3%, about 5%, or about 6% by weight of the composition.

In another embodiment described herein, three or more essential oils comprise rosemary oil having a weight percentage of about 0.5% to about 5% by weight of the composition. In one embodiment, the rosemary oil comprises about 0.75% to about 4%, about 1% to about 3.5%, or about 1.25% to about 3% by weight of the composition. In one aspect, the rosemary oil comprises about 0.5%, about 1%, about 1.5%, about 2%, about 2.5%, about 3%, about 3.5%, about 4%, about 4.5%, or about 5% by weight of the composition. In one aspect, the rosemary oil comprises about 2% by weight of the composition. In one aspect, the rosemary oil comprises about 1%, about 3%, about 4%, or about 5% by weight of the composition.

In another embodiment described herein, three or more essential oils comprise clove oil having a weight percentage of about 1% to about 5% by weight of the composition. In one embodiment, the clove oil comprises about 1% to about 4%, about 1% to about 3.5%, about 1% to about 3%, or about 1% to about 2.5% by weight of the composition. In one aspect, the clove oil comprises about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5% by weight of the composition. In one aspect, the clove oil comprises about 1% by weight of the composition. In another aspect, the clove oil comprises about 1%, about 2%, or about 3% by weight of the composition.

In another embodiment described herein, three or more essential oils comprise camphor having a weight percentage of about 0.5% to about 5% by weight of the composition. In one embodiment, the camphor comprises about 0.75% to about 4.5%, about 1% to about 4%, or about 1.5% to about 3.5% by weight of the composition. In one aspect, the camphor comprises about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5% by weight of the composition. In one aspect, the camphor comprises about 2% by weight of the composition. In another aspect, the camphor comprises about 1%, about 3%, or about 4% by weight of the composition.

In another embodiment described herein, three or more essential oils comprise methyl salicylate having a weight percentage of about 1% to about 8% by weight of the composition. In one embodiment, the methyl salicylate comprises about 0.75% to about 7%, about 1% to about 6%, or about 1.25% to about 5% by weight of the composition. In one aspect, the methyl salicylate comprises about 1%, about 2%, about 3%, about 4%, about 5%, about 6%, about 7%, or about 8% by weight of the composition. In one aspect, the methyl salicylate comprises about 5% by weight of the composition. In another aspect, the methyl salicylate comprises about 3%, about 4%, or about 6% by weight of the composition. In another embodiment described herein, the composition comprises one or more active agents. In one embodiment, active agents comprise capsaicin, diclofenac, ketamine, gabapentin, magnesium salicylate, acetylsalicylic acid or combinations thereof.

In another embodiment described herein, the one or more active agents comprise a weight percentage of about 5% to about 15% by weight of the composition. In one embodiment, the active agent comprises about 7.5% to about 14%, or about 10% to about 13% by weight of the composition. In one aspect, the active agent comprises about 5%, about 7%, about 9%, about 11%, about 13%, or about 15% by weight of the composition.

In another embodiment described herein, the ratio of carrier oil to essential oils comprises about 0.5:1 to about 1:1, including each ratio within the specified range. In one embodiment, the ratio of carrier oil to essential oils comprises about 0.5:1, about 0.6:1, about 0.7:1, about 0.8:1, about 0.9:1, or about 1:1. In one aspect, the ratio of carrier oil to essential oils comprises about 0.8:1. In one aspect, the ratio of carrier oil to essential oils comprises about 0.7:1. In one aspect, the ratio of inert carrier oil to essential oils is about 0.4:1, about 0.5:1, about 0.6:1, or about 0.9:1.

In another embodiment described herein, the ratio of coconut oil to rosemary oils comprises about 0.5:1 to about 50:1, including each ratio within the specified range. In one embodiment, the ratio of coconut oil to rosemary oil comprises about 0.5:1, about 1:1, about 5:1, about 10:1, about 15:1, about 20:1, about 25:1, about 30:1, about 35:1, about 40:1, about 45:1, or about 50:1. In aspect, the ratio of coconut oil to essential oils comprises about 16:1. In one aspect, the ratio of coconut oil to rosemary oil is about 15:1, about 17:1, or about 18:1.

In one embodiment, the compositions described herein have a rapid onset of analgesia after application. In one embodiment, the onset time comprises 0.5 seconds to about 2 hours, including all integers of time within the specified range. In one embodiment the onset time comprises about 0.5 seconds, about 1 seconds, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1 hour, or about 2 hours.

Also described herein are methods for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising administering to a subject in need thereof a composition as described herein.

Another embodiment described herein is a means for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising administering to a subject in need thereof a composition as described herein.

Another embodiment described herein is a composition useful for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition as described herein.

Another embodiment described herein is a use for treating, retarding the progression of, prophylaxis of, delaying the onset of, ameliorating, reducing the symptoms of, including but not limited to of one or more of cold, pain, inflammation, muscle twitch, muscle burn, fatigue, Sacroiliac Joint Arthropathy, Costochondritis, Competent syndrome, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition as described herein.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

Chronic musculoskeletal pain is relatively common in all age groups and may be the result of work-related trauma, sports-related injuries, postural events, various traumas and the natural aging process. Pharmaceutical agents including non-steroidal anti-inflammatory drugs acetaminophen, opioids and other drugs are frequently used to treat such patients. Because of the potential adverse effects associated with most of these drugs, one embodiment of the present invention, a topical analgesic, with coconut oil as a base ingredient and other natural oils, was clinically tested to determine its efficacy in the management of chronic musculoskeletal pain. A randomized, double-blind placebo-controlled study was done in St. Lucia with Embodiment #1 (Test drug), Diclofenac ointment (FDA-approved NSAID), and a placebo (Jasmine oil).

One hundred ninety six (196) patients were enrolled in the study. The patients were randomized to the 3 groups using the nQuery Advisor version 7.0 software protocol. All groups including Embodiment #1 showed a significant decrease in pain both after 2 and 4 weeks and there was no statistical significance between the 3 groups. However, the Embodiment #1 group continued to use the drug long after the official end of the study compared to the Diclofenac and placebo groups. This suggests that Embodiment #1 may have been more effective in controlling the pain. Another interesting observation was that patients in the Embodiment #1 group appeared to experience a relatively rapid onset of analgesia after application. Further, both the Diclofenac and Placebo groups developed adverse events, while patients receiving Embodiment #1 did not experience any adverse effects or complications. These results suggest that Embodiment #1 may be a useful tool in the armamentarium of providers treating patients with chronic musculoskeletal pain.

Methods

The objective of this study was to assess the analgesic efficacy of Embodiment #1 for the management of chronic musculoskeletal pain. After obtaining permission from the Committee for the Protection of Human Subjects attached to the St. Lucia Pain Institute, the Ministry of Health in St. Lucia and the St. Lucia Medical and Dental Association Ethics Committee, a randomized, double-blind, placebo-controlled study was designed and implemented in the Caribbean island of St. Lucia. St. Lucia was chosen as the study site for a number of reasons: that population is relatively opioid-naive; chronic musculoskeletal pain is quite common, and most patients tend to use and in some cases, prefer to use topical analgesics for musculoskeletal pain management instead of oral or other parenteral medications. Moreover, the Principal Investigator (inventor of the present invention) lives in St. Lucia for part of the year. One hundred and ninety-six (196) patients were enrolled in the study and were subsequently randomized to a pre-determined computerized protocol. The randomized protocol used was the nQuery Advisor version 7.0 software (copyright 2007 Janet-D-Elashoff).(14) The patients were assigned to one of three groups: the Placebo group; the Embodiment #1 group and the Diclofenac group. Diclofenac, a well-known FDA-approved and commonly used Non-Steroidal Anti-Inflammatory drug was used as a topical ointment while both the placebo and the study drug Embodiment #1 were dispensed in liquid form in a blue bottle (to prevent drug degradation by sunlight) with a pump-spraying device attached. The placebo used in the study was Jasmine oil, which has a medicinal smell but has no analgesic or anti-inflammatory properties. The Diclofenac ointment was dispensed in a label-less tube.

The present inventor recognized that there was a difference between the tube and the bottle with a pump-spray device, but thought that difference in containers would not affect the outcome unless patients were able to meet and compare study medications amongst themselves. The present inventor believed this comparison amongst patients unlikely since patients were recruited from all over the island and were not confined to a restricted geographical area.

All patients were initially evaluated by the Principal Investigator and another investigator after triage screening by the Study Coordinator. At that screening, the patients were assessed using the inclusionary and exclusionary criteria. All patients selected for participation in the study were between 18 and 75 years of age; had chronic axial musculoskeletal pain; were not actively using any other analgesics including opioid drugs; had no severe diabetic or hypertensive illnesses; never had any spinal surgery and were relatively ambulatory as far as their activities of daily living were concerned. Of the patients evaluated, 6 were excluded from enrollment for various issues relating to the inclusionary and exclusionary criteria. Patients were recruited via television, radio and newspaper announcements, and interviews announcing the study. It is important to note that for a country where clinical studies and drug trials are not routinely carried out, the response was overwhelmingly positive. Enrollment of all 196 patients was completed in 11 days from the initial commencement of the study. This study was supported and funded by three St. Lucian Financial Institutions.

All patients' musculoskeletal pain was classified by anatomical location: Cervical (14), Thoracic (26), Lumbar (137) and Sacral-coccygeal (14). Subjective Pain Intensity Rating (SPIR) was determined on each patient using a scale of 0 (no pain) to 10 (the maximum possible pain, e.g. immersion of the hand in boiling water). That raw score was multiplied by 10 to obtain a percentage score. For example, if a patient was not precise and indicated that the pain was between 6 and 7, the patient was assigned a score of 65%. After successful enrollment, patients were randomized to one of the 3 groups. Patients were dispensed with 5 ounces of one of the 3 medications and were instructed to apply the medication twice daily for 2 weeks.

Patients were instructed by the study coordinator in the technique for application and use of the various medicines to the painful site. All patients signed Study Consent Forms and were given additional written instructions regarding the application of medication to the painful site and also other precautionary warnings regarding the use and handling of the medicines eg protection for the eyes, etc. Patients were also given telephone numbers of the Study Coordinator and Principal Investigator to be used in case of an emergency. From a demographic perspective, 97% of patients were Black, 2.5% were Indian and 0.5% were Caucasian. 63% were females and 37% were males.

Overall, the mean (SD) age was 52 (12.7) years; within groups it was 50.5, 53.3, and 52.2 for placebo, Embodiment #1, and Diclofenac groups respectively. Average SPIR pain at baseline was 65.5, 68.8, and 67.3% for placebo, Embodiment #1, and Diclofenac groups respectively.

There was no significant difference among the treatment groups with respect to race (P=0.4548), gender (P=0.6170), age (P=0.4538), or baseline pain (P=0.4538).

All patients were contacted by the Study Coordinator after 2 weeks and pain score (as described above), satisfaction with the drug, satisfaction with the overall study and the presence of adverse effects were determined. Then, 2 weeks later (4 weeks after study commencement), patients were asked to return to the study office (St. Lucia Pain Institute office) for follow-up clinical evaluation and determination of pain score, adverse effects and related data similar to what was obtained at 2 weeks. Further, all patients were paid $50.00 EC to cover the costs of transportation to and from the study office at the beginning of the office and at the 4 week conclusion of the study.

During the study, there were 11 protocol violations: 5 patients who randomized to Embodiment #1 received placebo; 5 others who were randomized to placebo received Embodiment #1 and 1 patient who was randomized to Embodiment #1 received Diclofenac. These errors were due to a distribution/drug-storage mix-up which apparently occurred at random. When the error was recognized, the process was immediately corrected and there were no further protocol violations. As a result of those protocol violations, all analyses were conducted both on Intention-to-treat basis (as assigned) as well as-treated. Two (2) enrolled patients dropped out of the study before participation and they were both from the Diclofenac group; thus, there were 194 patients available for analysis at baseline. In addition, one (1) patient was not able to be contacted for both the 2nd week and 4th week follow-up interventions. A three (3) month follow-up telephone interview was conducted on the patients who were available. Of the original 196 patients, 152 were contacted and responded to a follow-up questionnaire which addressed continued pain and its score; continued use of the various study drugs and subsequent satisfaction with the individual drug.

Statistical Methods

The primary objective of the study was to determine pain responses to the three treatment drugs as defined by the change, that is the decrease or increase in reported SPIR score from baseline to follow-up at 2 weeks and at 4 weeks after baseline. As mentioned previously, the patients were randomized to 1 of 3 treatment groups, i.e. placebo, Embodiment #1, and Diclofenac groups using the nQuery Advisor version 7.0 software (copyright 2007, Janet D. Elashoff).

The three randomized treatment groups were compared on these and other numeric outcomes with non-parametric Kruskal-Wallis rank tests due to the non-Gaussian nature of their data distributions. Categorical characteristics (race, gender) were compared with simple chi-squared tests. A sub-analysis was carried out on the set of patients with lumbar pain, and a confirmatory multivariable regression was performed to check the association of treatment and change in pain after adjusting for baseline pain, type of pain (lumbar vs other) and prior duration with pain. No adjustments were made for the multiple endpoints tested.

Results

The average SPIR pain score at enrollment was 65, 69, and 68% on a 100-point scale for placebo, Embodiment #1, and Diclofenac groups respectively. The mean SPIR pain score at enrollment was 65, 70, and 70 points on the same scale for placebo, Embodiment #1, and Diclofenac respectively. (Kruskal-Wallis P=0.3243). There was no significant difference among groups on magnitude of any pain scores or any change in pain scores, and this was the case in both the as-randomized analysis and the as-treated analysis.

All 3 groups showed significant decreases in pain scores from baseline to 2 weeks and to 4 weeks (all p<0.0001). Thus, although the Embodiment #1 group showed significant decreases in pain from baseline to both 2 weeks and 4 weeks, both the Diclofenac and the Placebo groups showed corresponding decreases in pain scores. The possible explanation for these findings will be discussed hereinbelow. The mean duration of pain prior to commencing the study for all patients was 9.88 years with a standard deviation of 10.47 years and a median of 6.0 years. There was no significant difference among groups in duration of prior pain with group medians of 4.0, 8.25, and 7.5 years for placebo, Embodiment #1, and Diclofenac groups respectively (P=0.1511). Overall, 94.7% of patients (177/187) reported prior musculo-skeletal pain of 6 months duration or longer, with 93.7%, 93.6%, and 96.8% for placebo, Embodiment #1, and Diclofenac groups respectively (exact p=0.7759).

As far as the relationship between the magnitude of the pain and the duration of prior pain was concerned, there was no correlation between those two parameters. The smallest correlation was P=0.1237. With regard to the location of the musculo-skeletal pain, lumbar pain was the dominant type of pain as reported by 69.6% of the patients (137/196). The percentage of lumbar pain was closely similar among the 3 treatment groups: 72.3% for the placebo group; 71.9% for the Embodiment #1 group and 65.7% for the Diclofenac group (p=0.6482). Since over two thirds of the enrolled patients had lumbar musculo-skeletal pain, there was a sub-analysis of that group and in that subset too, there was no significant difference among groups on the magnitude of pain scores, change in pain scores or in pain satisfaction. The smallest correlation was p=0.3628. All 3 groups in this subset of patients showed significant decreases in pain from baseline to 2 weeks and to 4 weeks. (all p<0.0001).

In the multivariable ANCOVA adjusted for level of pain at baseline, type of pain (lumbar vs other) or duration of pain, there was no significant effect of treatment or change in pain at 2 or 4 weeks.

As far as side effects or complications were concerned, none of the patients taking Embodiment #1 experienced any adverse effects. Four patients in the Diclofenac group and two in the placebo group developed superficial skin rashes which receded without therapy when the drug was discontinued. However, all patients were able to complete the study. One patient in the Diclofenac group, admitted that she was obtaining satisfactory pain relief from Diclofenac application but after 5 days, she developed progressive radicular pain and paresthesiae which were intensifying. These sensations subsided when the medication was discontinued but promptly reappeared when the Diclofenac was re-introduced. This was considered a major adverse effect of Diclofenac and the study was discontinued in that patient after 8 days although the patient was obtaining satisfactory pain relief from the drug. None of the patients who developed adverse effects required any medical interventions for the treatment of these effects.

It is interesting to note that none of the patients in the Embodiment #1 group experienced any side effects or complications, while a few patients in both the placebo and the Diclofenac group experienced side effects and complications. Three (3) months after the completion of the study, an attempt was made to contact all the patients who participated in the study to assess the following: 1) the average pain score in the 3 months following the conclusion of the study; 2) the change in pain score from baseline to the 3 month post study period; 3) Pain score at the 3 month post-study period; and 4) Continued use of Embodiment #1, Placebo, and Diclofenac from the official conclusion of the study to the 3 month post-study period. Permission was obtained from the CPHS to implement this addendum to the study.

Of the 196 patients who were initially enrolled in the study, not all were available for the 3 month post-study telephone interviews. It is important to point out that this was not the patient responsibility or contractual duty to participate in this addendum to the study. Only 152 subjects from the originally enrolled ones were contacted for that 3 month post-study telephone interview. Fifty-four (54) Embodiment #1 patients, fifty-three (53) Diclofenac, and forty-five (45) Placebo patients were contacted and they responded to the 4 questions asked. There was no difference among treatments in the 3 month post-study average pain score over the past 3 months, nor in the current pain score. Median pain score at 3 months was 20, 25, and 20% on a 100 point scale for Embodiment #1, Diclofenac, and Placebo groups respectively. Median change in pain from baseline to 3 months showed a decrease of 37.5%, 30%, and 40% on the 100 point scale for Embodiment #1, Diclofenac, and Placebo groups respectively. Median change in pain from baseline 3 months showed a decrease of 37.5%, 30%, and 40% on a 100 point scale for Embodiment #1, Diclofenac, and Placebo groups respectively. This decrease was not statistically significant. However, there was a significant difference among the groups with respect to the estimated time that subjects voluntarily continued their treatment application after the official end of the study. That median time interval was 13.5, 0.0, to 7.0 weeks for Embodiment #1, Diclofenac, and Placebo groups respectively (p<0.0001). That time period was significant and may reflect the long-term efficacy of Embodiment #1 compared to Diclofenac and Placebo. In other words, continued use of the drug may be indicative of continued satisfaction with its use while non-use might conversely reflect lack of analgesic efficacy or dissatisfaction with the drug. All the medications including placebo were dispensed in 5 ounce containers which barring spillage or wastage would last for several weeks. Another interesting observation was that patients in the Embodiment #1 group volunteered the information that Embodiment #1 appeared to work rapidly after application to the affected part of the body. This observation was not quantified since onset of action was not part of the original protocol.

Analysis

Whereas Embodiment #1, the study drug did show significant decrease in pain score in the patients who used it, there were comparable significant decreases in pain scores in both the Diclofenac and Placebo groups making the overall Embodiment #1 decrease not statistically significant. There are many possible reasons for this lack of statistical significance in the results. First, this was a relatively small study number (196 subjects) and this factor may be the overwhelming most important one. That number was influenced by the limited funding available for the project. Second, St. Lucia is a tropical paradise and a popular tourist destination. Clinical trials and Medical research projects are not usually conducted in St. Lucia. It was quite interesting to observe the great enthusiasm of the persons responding to the television, radio and newspaper notices announcing the study. The general observation was that respondents were very excited and proud to participate in this particular clinical trial; it was also clear that participants were thrilled that local products especially coconut oil were a major ingredient of the study drug and this may have evoked some national pride, enthusiasm and possible bias. Third, there was study violation which impacted 11 patients (5 from the Embodiment #1 group, 5 from the Placebo group and 2 from the Diclofenac group). As a result of those distributional errors, all analyses were conducted both on an as assigned intention-to-treat basis as well as on an as-treated basis. Neither analysis showed any statistical significance in the decreases in pain score at this 2 and 4 week intervals. Thus, it was concluded that the study violation did not affect the results or outcome of the study.

The fact that the Embodiment #1 group continued using their medication for a median interval of 13.5 weeks after the official end of the study possibly suggests that these patients were obtaining significant analgesic benefit over the long term. None of the Diclofenac patients used their drug after the official conclusion of the study at 4 weeks. An inference could be made that those patients may not have been motivated to continue using Diclofenac because of lack of efficacy or for some other reason. Patients in the Placebo group continued using their drug for 7 weeks after the official conclusion of the study.

Prophetic Example 2

An exemplary composition useful for treating musculoskeletal pain as described herein is shown in Table 5. Composition components are set forth by weight percentage of the total mass of the composition.

TABLE 5

Exemplary Musculoskeletal Topical Composition

| Component | Exemplary Component | Weight Percentage (%) |
|---|---|---|
| Carrier | Mineral Oil | 36 |
| Essential Oils | Refined Coconut Oil | 36 |
| | Eucalyptus Oil | 3 |
| | Nutmeg Oil | 2 |
| | Rosemary Oil | 5 |
| | Clove Oil | 5 |
| | Camphor | 5 |
| | Methyl Salicylate | 8 |
| TOTAL | | 100% |

Prophetic Example 3

An exemplary composition useful for treating musculoskeletal pain as described herein is shown in Table 6. Composition components are set forth by weight percentage of the total mass of the composition.

TABLE 6

Exemplary Musculoskeletal Topical Composition

| Component | Exemplary Component | Weight Percentage (%) |
|---|---|---|
| Carrier | Mineral Oil | 45 |
| Essential Oils | Refined Coconut Oil | 45 |
| | Eucalyptus Oil | 1 |
| | Nutmeg Oil | 2 |
| | Rosemary Oil | 0.5 |
| | Clove Oil | 1 |
| | Camphor | 2 |
| | Methyl Salicylate | 3 |
| TOTAL | | 100% |

Prophetic Example 4

An exemplary composition useful for treating musculoskeletal pain as described herein is shown in Table 7.

Composition components are set forth by weight percentage of the total mass of the composition.

TABLE 7

Exemplary Musculoskeletal Topical Composition

| Component | Exemplary Component | Weight Percentage (%) |
|---|---|---|
| Carrier | Mineral Oil | 38 |
| Essential Oils | Refined Coconut Oil | 37 |
| | Eucalyptus Oil | 8 |
| | Nutmeg Oil | 6 |
| | Rosemary Oil | 2 |
| | Clove Oil | 3 |
| | Camphor | 1 |
| | Methyl Salicylate | 5 |
| TOTAL | | 100% |

Prophetic Example 5

An exemplary composition useful for treating musculoskeletal pain as described herein is shown in Table 8. Composition components are set forth by weight percentage of the total mass of the composition.

TABLE 8

Exemplary Musculoskeletal Topical Composition

| Component | Exemplary Component | Weight Percentage (%) |
|---|---|---|
| Carrier | Mineral Oil | 41 |
| Essential Oils | Refined Coconut Oil | 41 |
| | Eucalyptus Oil | 5 |
| | Nutmeg Oil | 4 |
| | Rosemary Oil | 3 |
| | Clove Oil | 1 |
| | Camphor | 3 |
| | Methyl Salicylate | 2 |
| TOTAL | | 100% |

Prophetic Example 6

An exemplary composition useful for treating musculoskeletal pain as described herein is shown in Table 9. Composition components are set forth by weight percentage of the total mass of the composition.

TABLE 9

Exemplary Musculoskeletal Topical Composition

| Component | Exemplary Component | Weight Percentage (%) |
|---|---|---|
| Carrier | Mineral Oil | 43 |
| Essential Oils | Refined Coconut Oil | 42 |
| | Eucalyptus Oil | 2 |
| | Nutmeg Oil | 5 |
| | Rosemary Oil | 1 |
| | Clove Oil | 1 |
| | Camphor | 5 |
| | Methyl Salicylate | 1 |
| TOTAL | | 100% |

Prophetic Example 7

An exemplary composition useful for treating musculoskeletal pain as described herein is shown in Table 10. Composition components are set forth by weight percentage of the total mass of the composition.

TABLE 10

Exemplary Musculoskeletal Topical Composition

| Component | Exemplary Component | Weight Percentage (%) |
|---|---|---|
| Carrier | Mineral Oil | 39 |
| Essential Oils | Refined Coconut Oil | 41 |
| | Eucalyptus Oil | 6 |
| | Nutmeg Oil | 3 |
| | Rosemary Oil | 0.5 |
| | Clove Oil | 1 |
| | Camphor | 4 |
| | Methyl Salicylate | 6 |
| TOTAL | | 100% |

Prophetic Example 8

In a continuing effort to effectively treat acute and chronic musculoskeletal pain, additional work is planned to further explore the efficacy of natural essential oils in accomplishing that task. In a previous randomized, double-blind, placebo-controlled clinical trial performed by the inventor and his associates using Embodiment #1 as the test drug, the trial demonstrated that Embodiment #1 was effective in controlling chronic musculoskeletal pain. However, that pain control was not statistically significant when compared to Diclofenac and placebo. There were many possible reasons (discussed hereinabove) for these findings. Nevertheless, the study did show that Embodiment #1, unlike placebo and Diclofenac was safe and free of side effects, and had a rapid onset of action of less than 30 minutes. In an attempt to further evaluate the analgesic efficacy of these natural essential oils in controlling chronic musculoskeletal pain, one or both of Embodiments #2 and #3, which contain additional essential oils, will be used as the test composition for a second clinical study.

Embodiments #2 and #3 are different from Embodiment #1 in two ways: 1) an additional essential oil which is not present in Embodiment #1; and 2) the other ingredients have varying percentages as compared to Embodiment #1. Thus, the objective of the second clinical study is to evaluate the clinical efficacy of one or more of Embodiment #2 and #3 as a topical analgesic for managing acute and chronic musculoskeletal pain. The test composition will be one or more of Embodiment #2 or #3, and jasmine oil will be used as the placebo. Diclofenac gel or Pennsaid drops would be used as the known topical NSAID drug.

This study will differ from the Embodiment #1 study in the following ways:

1) The number of subjects enrolled in each of the 3 groups will be increased from 196 to 500 in order to increase the robustness of the study;

2) Patients with both Acute and Chronic pain syndromes will be evaluated as 2 separate groups: a. Acute Pain Syndrome (pain present for less than 6 weeks); and b. Chronic Pain Syndrome (pain present for more than 6 weeks);

3) The study period will increase from four weeks for the first part of the study to 8 weeks in the case of the chronic pain group in order to obtain a comprehensive set of data. The study protocol would remain the same for patients with Acute Pain Syndrome, i.e. there would be three patient encounters;

4) To increase patient contacts from 3 encounters to 5 encounters. (Initial visit; at 2 weeks; at 4 weeks; at 6 weeks and at 8 weeks or final visit with the second and the fourth encounters being telephone assessments;

5) To incorporate a specific assessment tool for measuring onset of action of the various drugs in the study. Studies may include pain measurements using commonly used pain intensity scales such as the Visual Analog Scale for Pain (VAS) or the Subjective Pain Intensity Rating (SPIR);

6) Since one or more of Embodiments #2 or #3 are an OTC topical analgesic, no toxicology studies would be required initially.

Methods

Qualified patients would be enrolled into the Acute Pain Group or the Chronic Pain Group and then randomly assigned into one of the 3 groups of the study using a randomized predetermined computerized protocol. The groups would be as follows: a) placebo group receiving jasmine oil; b) test study with one or more of Embodiments #2 or #3; and c) known NSAID Diclofenac drug or Pennsaid Drops. Patient recruitment would come from Duke Primary Care practices, Duke Sports Medicine Centers, the Center for Living at Duke University, Duke Integrative Medicine Center and from various Pain Clinics whose patients would not be prescribed with any opioid medications during the study duration.

Enrollment Criteria

The following inclusionary and exclusionary enrollment criteria will apply to the study:

Inclusionary Criteria

1) Patients with acute and chronic musculo-skeletal pain including Myofascial Pain Syndrome, Osteoarthritis, Degenerative Joint Disease, Fasciitis, Tendonitis, Carpal Tunnel Syndrome, Non-specific Chronic Lower Back pain, sprains, strains, athletic injuries with without fractures or neuro-vascular pathology, ligamentous injuries, Tarsal Tunnel Syndrome and Plantar Fasciitis;

2) Patients between 18 to 80 years old; and

3) Patients of all races, gender, ethnicity and sexual orientation.

Exclusionary Criteria

1) Patients with spinal cord injuries, spinal nerve lesions, cancer or skin disorders would be excluded;

2) Patients with severe and uncontrolled hypertension, chronic gastro-intestinal disorders and severe and uncontrolled diabetes mellitus would be excluded;

3) Patients with skin rashes or skin irritation at the painful site would be excluded; and 4) Patients on opioids or NSAIDs of any kind would be excluded.

After selection, patients will undergo a history and physical examination and a diagnosis or series of diagnoses will be established. The patient will then be blindly assigned to a group using a randomized predetermined computerized protocol. At that time, informed consent would be obtained; appropriate signatures for consent obtained and the assigned drug dispensed to the patient. The patient at that point would be instructed regarding the application and usage of the assigned drug which would be applied twice a day.

Duration of Study

The total duration of the study for the Acute Pain Group is 4 weeks. All patients in this group would take the medication as prescribed for 4 weeks. Patients would be evaluated and pain score recorded at enrollment and at the end of 4 weeks. The patients would also be assessed for adverse effects and complications. After 2 weeks of enrollment in the study, a telephone encounter would occur at which time patients would assessed for adverse effects and complications and pain score would be obtained.

The total duration of the study for the Chronic Pain Group is 8 weeks. All patients in this group would have a baseline pain score determination at enrollment and at 2 weeks, 4 weeks, 6 weeks and at 8 weeks. The initial encounter, 4 weeks and 8 weeks encounter would be at the study office by the PI or his designated associate. The encounters at 2 weeks and 6 weeks would be telephone events. At each encounter, pain score and adverse event or complication reporting would be sought. A suitable tool for assessing onset of action would be used and it would be utilized in all patients during the initial evaluation.

Assessments

Using the Subjective Pain Intensity Rating (SPIR) on a scale of 0 (no pain) to 10 (maximum pain like putting the hand in boiling water) the patient's pain in all 3 groups of the Acute Pain Group would be assessed at: a) initial visit and start of study; b) 2 weeks after beginning study; and c) 4 weeks after beginning study.

The Chronic Pain group would be assessed at: a) initial visit and start of study; b) 2 weeks after enrollment; c) 4 weeks after enrollment; d) 6 weeks after enrollment; e) 8 weeks after enrollment.

All patients will be assessed for side effects, adverse effects and any other complications at 2 weeks and 4 weeks respectively. Patient will be advised to discontinue medication should side effects or complication occur and that they should contact the Study Coordinator. All results will be collected, collated and stored by the Project Coordinator.

Statistical Analysis

All the data collected will be sent to Duke University Department of Anesthesiology for appropriate statistical analysis. Results and conclusions will be formulated based on the analyses. After reviews of the results and statistical analyses, it will be determined if one or more of Embodiments #2 or #3 is as good as, better, or less effective than the other two test drugs or placebo, as a topical analgesic agent. Review of the side effects, adverse effects and complications will be done to determine efficacy and safety of one or more of Embodiments #2 or #3 compared to the other two agents and the placebo. Further, onset of action of one or more of Embodiments #2 or #3 would be assessed compared to placebo and Diclofenac gel or Pennsaid drops.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A composition for musculoskeletal pain, wherein the composition comprises:
   (a) about 35-45% mineral oil;
   (b) about 35-45% refined coconut oil;
   (c) about 1-8% eucalyptus oil;
   (d) about 1-10% nutmeg oil;
   (e) about 0.5-5% rosemary oil;
   (f) about 0.5-5% camphor; and
   (g) about 1-8% methyl salicylate;
   wherein the combined effect of the composition results in rapid onset pain relief.

2. The composition of claim 1, further comprising one or more additional essential oils selected from one or more of agar oil, ajwain oil, angelica root oil, anise oil, asafoetida, Balsam of Peru, basil oil, bay oil, Bergamot oil, black pepper, birch oil, camphor, cannabis flower, caraway oil, cardamom seed oil, carrot seed oil, cedarwood oil, chamomile oil, calamus Root, cinnamon oil, cinnamon cassia, cistus species, citron, citronella oil, clary sage, clove leaf oil, coffee, coriander, costmary oil, costus root, cranberry seed oil, cubeb, cumin oil/black seed oil, cypress, cypriol, curry leaf, davana oil, dill oil, elecampane, fennel seed oil, fenugreek oil, fir, frankincense oil, galangal, galbanum, geranium oil, ginger oil, goldenrod, grapefruit oil, henna oil, helichrysum, hickory nut oil, horseradish oil, hyssop, Idaho tansy, jasmine oil, juniper berry oil, laurus nobilis, lavender oil, ledum, lemon oil, lemongrass, lime, litsea cubeba oil, linaloe, mandarin, marjoram, melaleuca, Melissa oil, mentha arvensis oil/mint oil, moringa oil, mountain savory, mugwort oil, mustard oil, myrrh oil, myrtle, neem oil, Neem Tree Oil, neroli, orange oil, oregano oil, orris oil, Palo Santo, parsley oil, Patchouli oil, Perilla essential oil, peppermint oil, petitgrain, pine oil, Ravensara, Red Cedar, Roman Chamomile, rose oil, rosehip oil, rosewood oil, sage oil, sandalwood oil, sassafras oil, savory oil, Schisandra oil, spearmint oil, spikenard, spruce, star anise oil, tangerine, tarragon oil, tea tree oil, thyme oil, Tsuga, turmeric, valerian, vetiver oil, Western Red Cedar, wintergreen, ylang-ylang, zedoary, or combinations thereof.

3. The composition of claim 1, further comprising an active agent ingredient selected from one or more of capsaicin, diclofenac, magnesium salicylate, acetylsalicylic acid, or combinations thereof.

4. The composition of claim 1, further comprising about 1-5% clove oil.

5. The composition of claim 1, wherein the composition comprises:
 (a) about 40% mineral oil;
 (b) about 40% refined coconut oil;
 (c) about 4% eucalyptus oil;
 (d) about 5.61% nutmeg oil;
 (e) about 2.41% rosemary oil;
 (f) about 1% clove oil;
 (g) about 2.41% camphor; and
 (h) about 4.81% methyl salicylate.

6. The composition of claim 1, wherein the composition comprises:
 (a) about 38.9% mineral oil;
 (b) about 40.3% refined coconut oil;
 (c) about 4% eucalyptus oil;
 (d) about 5.61% nutmeg oil;
 (e) about 2.41% rosemary oil;
 (f) about 1.6% clove oil;
 (g) about 2.41% camphor; and
 (h) about 4.81% methyl salicylate.

7. The composition of claim 1, wherein the ratio of mineral oil to other oils of the composition comprises from about 0.5:1 to about 1:1.

8. The composition of claim 1, suitable for topical application.

9. The composition of claim 1, wherein the ratio of coconut oil to rosemary oil is from about 16:1 to 17:1.

10. The composition of claim 1, wherein the composition includes six or more essential oils.

11. A method for treating, retarding the progression of, prophylaxis of, delaying the onset of, ameliorating, reducing the symptoms of cold, pain, inflammation, muscle twitch, muscle burn, fatigue, Sacroiliac Joint Arthropathy, Costochondritis, Carpal Tunnel Syndrome, sports related injuries, Degenerative Joint Disease, Degenerative Disc Disease, Osteoarthritis, muscle, tendon or ligament trauma, post Chikungunya Syndrome, tendonitis, muscular strains and sprains, myofascial pain syndrome, or fasciitis comprising topically administering to a subject in need thereof a composition of claim 1.

* * * * *